United States Patent [19]

Wilkerson

[11] Patent Number: 5,278,162
[45] Date of Patent: Jan. 11, 1994

[54] 3,3'-DISUBSTITUTED-1,3-DIHYDRO-2H-PYRROLO[2,3-B]HETEROCYCLIC-2-ONE USEFUL IN THE TREATMENT OF COGNITIVE DISORDERS OF MAN

[75] Inventor: Wendell W. Wilkerson, New Castle, Del.

[73] Assignee: The Du Pont Merck Pharmaceutical Company, Wilmington, Del.

[21] Appl. No.: 947,152

[22] Filed: Sep. 18, 1992

[51] Int. Cl.$^5$ .................. A61K 31/50; A61K 31/505; A61K 31/44; C07D 471/04

[52] U.S. Cl. ..................................... 514/252; 514/254; 514/255; 514/256; 514/269; 514/300; 544/238; 544/298; 544/322; 544/333; 544/336; 544/405; 546/113

[58] Field of Search ............... 544/298, 238, 333, 322, 544/405, 236, 280, 350, 336; 546/113; 514/252, 254, 255, 256, 300, 269

[56] References Cited

U.S. PATENT DOCUMENTS

| | | | |
|---|---|---|---|
| 4,760,083 | 7/1988 | Myers et al. | 544/296 |
| 4,997,954 | 3/1991 | Fortunak | 548/486 |
| 5,006,537 | 4/1991 | Effland et al. | 546/15 |

FOREIGN PATENT DOCUMENTS 8912637 12/1989 World Int. Prop. O. .......... 546/113

Primary Examiner—John M. Ford
Assistant Examiner—Y. N. Gupta
Attorney, Agent, or Firm—Gildo E. Fato

[57] ABSTRACT

Compounds of Formula I have been shown to enhance the release of the neurotransmitters acetylcholine, dopamine and serotonin; and thus may be useful in the treatment of diseases of man where subnormal levels of this neurochemical are found such as in Alzheimer's disease and other conditions involving learning and cognition; and Parkinson's disease.

The compounds of this invention can be described as shown in Formula I

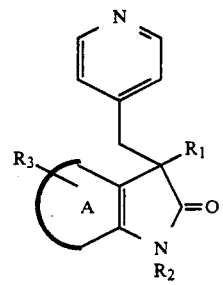

Formula I where A is a heteroaromatic system.

22 Claims, No Drawings

3,3'-DISUBSTITUTED-1,3-DIHYDRO-2H-PYRROLO[2,3-B]HETEROCYCLIC-2-ONE USEFUL IN THE TREATMENT OF COGNITIVE DISORDERS OF MAN

BACKGROUND OF THE INVENTION

1. Field of Invention

This invention relates to disubstituted polycyclic compounds, pharmaceutical compositions, processes for preparation, and methods of use in mammals to treat cognitive disorders and/or neurological dysfunction and/or mood disturbances such as, but not limited to degenerative nervous system diseases. Additionally, these compounds can be used as reagents in studies on the biochemical mechanism of neurotransmitter based diseases.

2. Background Including Prior Art

Increasingly there is a need for effective treatments for nervous system disorders and neurological deficiencies. Many of these diseases correlate with increasing age, due mainly to degenerative changes in the nervous systems. Although in early stages of some diseases certain systems are rather specifically affected (e.g. cholinergic systems in Alzheimer's Disease and Myasthenia Gravis, the dopaminergic system in Parkinson's Disease, etc.), multiple neurotransmitter system deficiencies (acetylcholine, dopamine, norepinephrine, serotonin) is generally found at later stages of disease such as senile dementia, multi-infarct dementia, Huntington's Disease, mental retardation, etc. This explains the generally observed multiple symptomatology that includes cognitive, neurological, and effective/psychotic components (see Gottfries, Psychopharmacol, 1985, 86, 245). Deficits in the synthesis and release of acetylcholine in the brain are generally thought to be related to cognitive impairment (see Francis, et al., New England J. Med., 1985, 7, 313) whereas neurological deficits (e.g. Parkinsonian symptoms) and mood/mental changes may be related to impairment of dopaminergic and serotonergic systems, respectively. Other neurological deficits (e.g. Myasthenia Gravis) are related to cholinergic deficiencies in the peripheral nervous system.

Treatment strategies employed previously encompass vasoactive drugs like vincamine and pentoxifylline; metabolic enhancers like ergoloid mesylates, piracetam, and naftidrofuryl; neurotransmitter precursors like 1-DOPA, choline, and 5-hydroxytryptamine; transmitter metabolizing enzyme inhibitors such as physostigmine; and neuropeptides like adrenocorticotropic hormone and vasopressin-related peptides. Except for 1-DOPA treatment for Parkinson's Disease and cholinesterase inhibitor treatment for Myasthenia Gravis, these treatment strategies have generally failed to enhance the residual function of the affected systems by enhancing the stimulus-induced release of neurotransmitters. Theoretically, such an enhancement would improve the signal-to noise ratio during chemical transmission of information, thereby reducing deficits in processes related to cognition, neurological function, and mood regulation.

The most pertinent literature citations and patent references related to this invention can be found in DeNoble, et al., Pharmacol. Biochem. Behavior, 1990, 36, 957; Cook, et al., 1990, 19, 301; Nickolson, et al., 1990, 19, 285; and Myers and Nickolson U.S. Pat. No. 4,760,083 (1988), and the references therein. These references describe and teach that a,a-disubstituted aromatic or heteroaromatic of the formula:

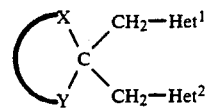

or a salt thereof wherein X and Y are taken together to form a saturated or unsaturated carbocyclic or heterocyclic first ring and the shown carbon in said ring is a to at least one additional aromatic ring or heteroaromatic ring fused to the first ring;

one of $Het^1$ or $Het^2$ is 2, 3 or 4-pyridyl; or 2, 4 or 5-pyrimidinyl, and the other is selected from
 (a) 2, 3 or 4-pyridyl
 (b) 2, 4 or 5-pyrimidinyl
 (c) 2-pyrazinyl
 (d) 3 or 4-pyridazinyl,
 (e) 3 or 4-pyrazolyl,
 (f) 2 or 3-tetrahydrofuranyl, and
 (g) 3-thienyl
are useful as cognition enhancers.

Patent WO 91/01/306, Feb. 7, 1991 discloses oxoindole derivatives of formula:

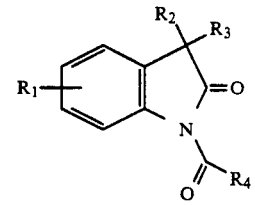

useful for treating senile dementia, i.e. improving brain functions and activating and protecting brain metabolism. In the above formula, $R^1$ represents hydrogen, halogen lower alkyl, or lower alkoxy; $R^2$ represents hydrogen or lower alkyl; $R^3$ represents —$CH_2$— $R^5$, wherein $R^5$ represents alkyl which maybe cyclic, benzodioxanyl, or phenyl which may be substituted with a plurality of hydrogen, lower alkyl, lower alkoxy, hydroxy, diethylamino, trifluromethyl, nitrile, nitro, or benzyloxy; alternatively $R^2$ and $R^3$ may be combined together to form =CH—$R^5$, wherein $R^5$ is defined above; and $R^4$ represents 1-propylbutyl, pyridyl, or phenyl or substituted phenyl.

EP 415102-A discloses a series of 1,3-dihydro-1-(pyridinylamino)-2H-indol-2-ones as having analgesic, anticonvulsant, and/or memory enhancing activity and are useful in the treatment of Alzheimer's disease.

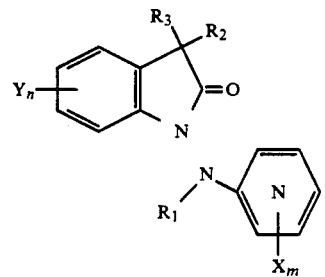

where $R^1-R^3 = H$, lower alkyl (opt. substd. by aryl); methyl or ethyl substituted by pyridyl of thienyl; or aryl; or $R^2+R^3$ completes 4-6 carbon cycloalkane or spiro fused arene, piperidine or tetrahydropyran;

X and Y=H, halo, lower alkyl, lower alkoxy, $NO_2$, $NH_2$, or $CF_3$;

m and n=1-3;

lower=1-6 carbon

Ting, et al., in EP 0347698 Al, described a series of heterobicyclic compounds having antiinflammatory activity with formula

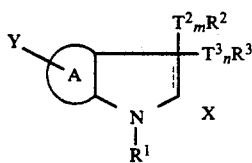

where A represents a fused 5- or 6-membered heterocyclic aromatic ring containing 1 to 3 heteroatoms in the ring, each heteroatom independently represents O, S, N or $NR^6$ where $R^6$ is the group $NR^6$ is H or $C_1$ to $C_4$ alkyl; the double lines represent optional double bond, such that when the bond to X is double, X is O or S; and when the bond to X is a single bond, X is $OR^{10}$ where $R^{10}$ is alkyl of aralkyl; $T^2$ and $T^3$ independently represent S, SO or $SO_2$; m and n independently represent 0 or 1; and $R^1$ is H, alkyl, aryl, or aralkyl; $R^2$ and $R^3$ independently represent H, alkyl, halogen, aryl or aralkyl, etc.

SUMMARY OF THE INVENTION

It has been found that certain polycyclic compounds having 'mixed pendant groups' gem substitutions enhance the stimulus-induced release of neurotransmitters, specifically acetylcholine, dopamine and serotonin in nervous tissues, and thus improve processes involved in learning and memorization of an active avoidance task.

Most particularly, according to the present invention there is provided a pharmaceutical composition consisting essentially of a pharmaceutically suitable carrier and an effective amount of a compound of the formula

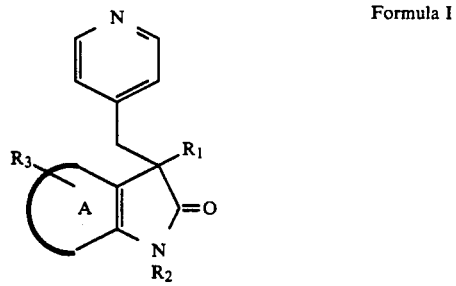

Formula I

Preferred Embodiment are compounds of Formula I where

A is

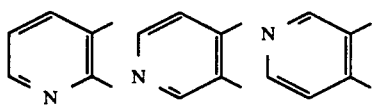

$R^1$ is $(CH_2)m-W$ or $(CH_2)n-R^4$;

$R^2$ is alkyl of 1-7 carbons, benzyl substituted with 0-3 $R^4$, or phenyl substituted with 0-3 $R^5$;

$R^3$ is H, alkyl of 1-6 carbons, halogen, CN, $OR^7$, $N(R^7R^8)$, $S(O)pR^7$, $NO_2$, or $CF_3$;

$R^4$ is $CO_2R^7$, $CON(R^7R^8)$, CN, $OR^7$, $N(R^7R^8)$, $S(O)pR^7$, F, Cl, Br, $NO_2$, or $COR^7$;

$R^5$ is $CO_2R^7$, $CON(R^7R^8)$, CN, $OR^7$, $N(R^7R^8)$, $S(O)pR^7$, F, Cl, Br, $NO_2$, $COR^7$, or $CF_3$;

$R^6$ is H, alkyl of 1-4 carbons, phenyl, or benzyl;

$R^7$ and $R^8$ independently are H, or alkyl of 1-6 carbons;

W is pyridyl, pyrimidinyl, pyrazinyl, pyridazinyl, pyrazolyl, tetrahydrofuranyl, thienyl, or phenyl optionally substituted with 0-2 $R^5$;

m is 1 to 4;

n is 1 to 6; and p is 0 to 2;

Most preferred compounds of Formula I are those where

A is

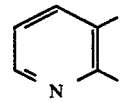

$R^1$ is $(CH_2)m-W$ or $(CH_2)n-R^4$;

$R^2$ is alkyl of 1-7 carbons, benzyl substituted with 0-3 $R^4$, or phenyl substituted with 0-3 $R^5$;

$R^3$ is H, alkyl of 1-4 carbons, halogen, CN, $OR^7$, $N(R^7R^8)$, $S(O)pR^7$, $NO_2$, or $CF_3$;

$R^4$ is $CO_2R^7$, $CON(R^7R^8)$, CN, $S(O)pR^7$, or $COR^7$;

$R^5$ is $CO_2R^7$, $CON(R^7R^8)$, CN, $OR^7$, $N(R^7R^8)$, $S(O)pR^7$, F, Cl, Br, $NO_2$, $COR^7$, or $CF_3$;

$R^6$ is H, alkyl of 1-4 carbons, phenyl, or benzyl;

$R^7$ and $R^8$ independently are H, or alkyl of 1-6 carbons;

W is pyridyl, pyrimidinyl, tetrahydrofuranyl;

m is 1 to 4;

n is 1 to 6; and p is 1 or 2.

Specifically preferred compounds of Formula I are:

a. 1,3-Dihydro-1-phenyl-3,3-bis(4-pyridinylmethyl)-H-pyrrolo[2,3-b]pyridin-2-one Dihydrochloride, b. 1,3-Dihydro-1-(4-chlorophenyl)-3,3-bis(4-pyridinylmethyl)-2H-pyrrolo[2,3-b]pyridin-2-one Dihydrochloride, c. 1,3-Dihydro-1-(4-chlorophenyl)-3-(3-cyanophenyl)-3-(4-pyridinylmethyl)-2H-pyrrolo[2,3-b]pyridin-2-one Dihydrochloride, d. 1,3-Dihydro-1-(4-chlorophenyl)-3-(3-pyridinylmethyl)-3-(4-pyridinylmethyl)-2H-pyrrolo[2,3-b]pyridin-2-one Dihydrochloride, e. 1,3-Dihydro-1-(4-chlorophenyl)-3-(phenylmethyl)-3-(4-pyridinylmethyl)-2H-pyrrolo[2,3-b]pyridin-2-one,

DETAILED DESCRIPTION OF THE INVENTION SYNTHESIS

Most of the compounds of this invention can be synthesized by the sequence shown in Schemes 1 and 2. Generally, when $R_1$ is 4-picolyl, the compounds are prepared as shown in Scheme 1, where the lactam IIA is reacted with excess 4-picolyl chloride under phase transfer conditions to give desired product. The phase transfer catalyst can be , but not limited to, tetrabutylammonium- iodide, chloride, or hydroxide. Depending on the facility of forming the anion at the 3-position of the lactam, IIA can be reacted with bases such as, but not limited to sodium or potassium bicarbonate, sodium or potassium carbonate, sodium, potassium, or lithium hydroxide, or any other base compatible with an organic-aqueous solvent system. The solvent system may be composed of water and an organic solvent which is not miscible with water such as but not limited to benzene, toluene, hexane, methyl cyclohexane, or methylene chloride. The reaction can be conducted at temperatures ranging from 4° C. to solvent reflux temperature. The reaction of IIA with excess 4-picolyl chloride can be conduct in non aqueous, aprotic solvents by forming the anion of IIA with excess bases such as, but not limited to, sodium or potassium hydride, n-butyl lithium, or sodium bis(trimethylsilyl) amide. The aprotic solvent can be, but not limited to, tetrahydrofuran, dioxane, dimethoxyethane, dimethylformamide, dimethyacetamine, or benzene.

Scheme 1. Synthesis of 3,3'-disubstituted-1,3-dihydro-2H-pyrrolo [2.3-b]heterocyclic-2-one when R¹ is 4-picolyl.

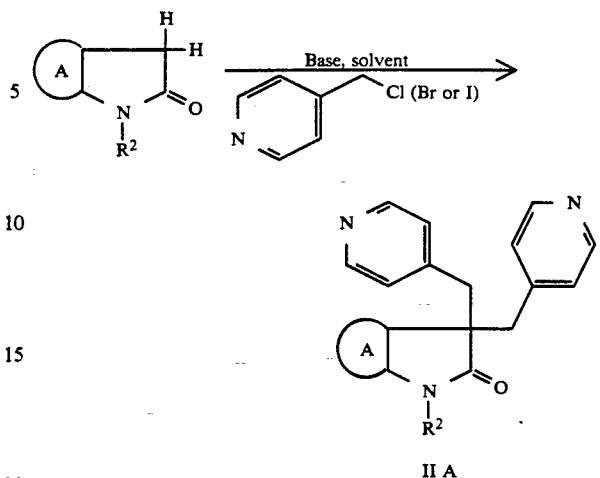

Scheme 2. Synthesis of 3,3'-disubstituted-1,3-dihydro-2H-pyrrolo[2,3-b]heterocyclic-2-one when R¹ is other than 4-picolyl.

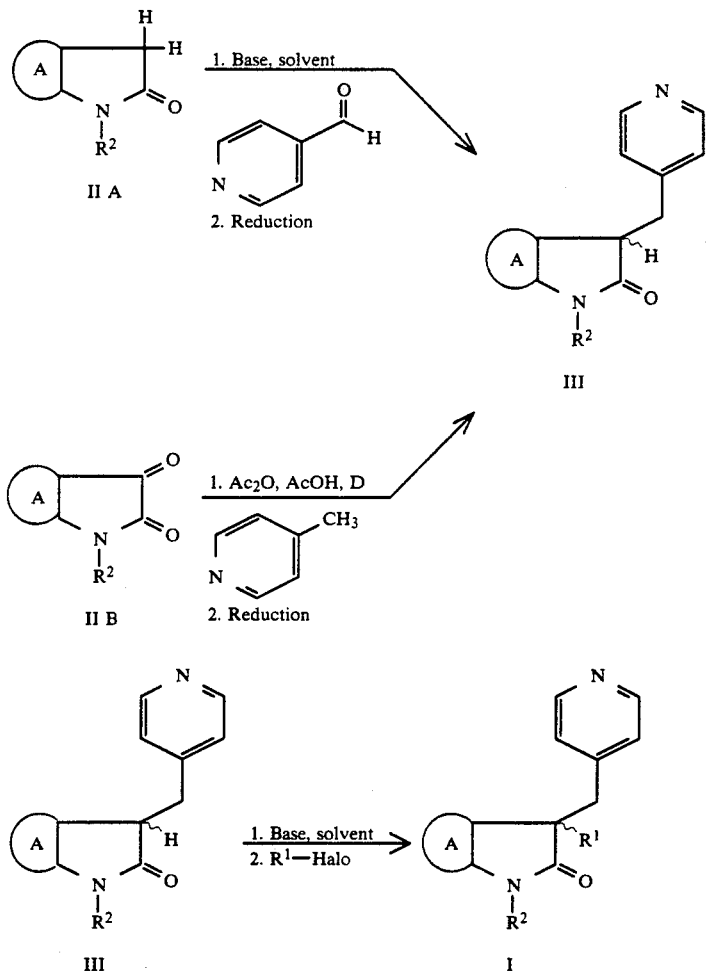

Alternatively, compounds of Formula I can be prepared by reacting III with strong bases such as but not limited to, sodium or potassium hydride, n-butyl lithium, or sodium bis(trimethylsilyl) amide in an aprotic solvent such as, but not limited to, tetrahydrofuran, dioxane, dimethoxyethane, dimethylformamide, dimethyacetamine or benzene. This approach can be seen in Scheme 2.

The starting lactam can be prepared as described by:
a. Marfat, et al., Tetrahedron Lett., 1987, 8(35); 4027–4030
b. R. P. Robinson and K. M. Donahue, J. Org. Chem., 1991, 56, 4805–4806
c. Ting, et al., J. Med. Chem., 1990, 33, 2697–2706;
d. Stingach, et al., Chemistry of Heterocyclic Compounds, 1981, 1, 54–56
e. Royer, et al., Tetrahedron, 1980, 36, 2499–2465
f. Schafer and Gewald, Monatsh. Chem., 1989, 120(4), 315–322
g. Wolfe, et al., J. Am. Chem. Soc., 1980, 102(10), 3646–3647
h. By using a combination of the method described by Taylor, et al., Tetrahedron, 1987, 43(21), 5145–5158, "Intramolecular Diels-Alder Reactions of 1,2,4-Triazines. A General Synthesis of Furo [2,3-b]-Dihydrppyrano[2,3-b]Pyridines, and Pyrrol[2,3]Pyridines", and the method described by Stingach, et al., Khimiya Geterotsiklicheskikh Soedinenii, 1981, 1, 54–56, "Thiosemicarbozones of 7-Azaisatin Derivatives" or the method described by Robinson and Donahue, J. Org. Chem., 1991, 56, 4805–4806, "Synthesis of 5-Azaoxindole", the desired starting materials could be made.
i. Fortunak, U.S. Pat. No. 4997954, 05 Mar 1992
j. Ting, et at., in EP 0347698 Al, and references therein.
k. Beugelmans and Roussi, Chem. Commun., 1979, 950
l. Goehring, Wolfe, et al., J. Am. Chem. Soc., 1985, 107, 435
m. Clark, et al., Synthesis (1991), 10, 871–878.

The compounds of this invention can exist as free bases or acid addition salts of pharmaceutically acceptable acids. Further, the compounds of this invention, where R[1] is other than 4-picolyl, can exist as racemates, or the separate enantiomers; diastereomers is R[1] contains a chiral center(s); or syn or anti or E or Z, or mixtures thereof if R[1] contains a moiety capable of forming geometric isomers.

SYNTHESIS

Preparation 1

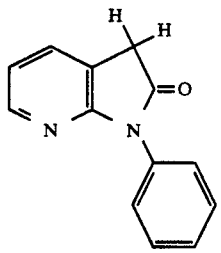

1,3-Dihydro-1-phenyl-2H-Pyrrolo[2,3-b]pyridin-2-one

The compound was prepared as described by Ting, Kaminski, et al., in "Substituted 1,3-Dihydro-2H-pyrrolo[2,3-b]pyridin-2-ones as Potential Antiinflammatory Agents", J. Med. Chem., 1990, 33, 2697–2706 in 55% yield; mp 116.0°–117.0° C.; IR(KBr): 1727 cm$^{-1}$ (CO); $^1$H NMR(CDCl$_3$ TMS): d 3.73 (s, 2H, CH$_2$—CO), [7.00 (dd, 1H), 7.39 (dd, 1H), 8.18 (d, 1H), 2,3-subs. Pyr], 7.51 (m, 5H, Phe); mass spec m/e 211 (M+1); Anal calcd for C$_{13}$H$_{10}$N$_2$O, MW 210.24: C, 74.27; H, 4.79; N, 13.33. Found: C, 74.11; 4.73; N, 12.92.

Other "heterocyclic" can be prepared using a modification of the teaching of Ting, et al., EP 0347698, 1989.

1,3-Dihydro-1-(4-chlorophenyl)-2H-pyrrolo[2,3-b]pyridin-2-one was prepared as taught in EP 0347698: mp 154°–155° C.; lit mp 148°–150° C.

EXAMPLE 1.

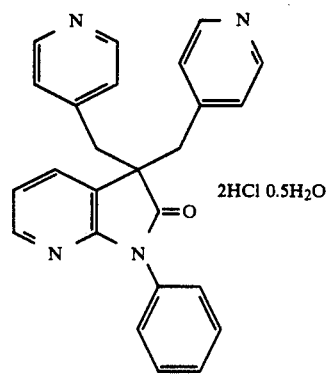

1,3-Dihydro-1-phenyl-3,3-bis(4-pyridinylmethyl)-2H-pyrrolo[2,3-b]pyridin-2-one Dihydrochloride Hemihydrate A suspension of NaH (0.55 g, 22.9 mmol) in 25 ml dry THF was treated with Prep 1 (1,3-dihydro-1-phenyl-H-pyrrolo[2,3-b]pyridin-2-one) (1.0 g, 4.76 mmol) and stirred under argon for 30 min at room temperature. The mixture was then treated with excess 4-picolyl chloride hydrochloride (2.5 g, 15.2 mmol) and stirred for and additional 3 h while under argon. The mixture was refluxed for 30 min, cooled to room temperature, and carefully partitioned between 200 ml CH$_2$Cl$_2$ and 200 ml water. The organic layer was washed with 2×100 ml water and brine, dried over MgSO$_4$, filtered, and concentrated to an oil which was found to be impure by TLC (CHCl$_3$—MeOH, 9:1). The oil was chromatographed on silica gel using CHCl$_3$—MeOH (9:1) as mobile phase. Appropriate fractions were combined and treated with 1N HCl/Et$_2$O, and concentrated at reduced pressure to give the desired product as an amorphous off-white solid in 37.7% (0.85 g) yield; mp 184.0°–185.0° C.; IR(nujol): 1716 cm$^{-1}$ (CO); $^1$H NMR(DMSOd$_6$ TMS): d, [3.67 (d, 2H), 3.76 (d, 2H), CH$_2$—C—CH$_2$)], [6.87 (d, 4H), 8.60 (d, 4H) two 4-Pyr], [7.38 (m, 1H), 8.00 (d, 1H), 8.20 (d, 1H), 2,3-disubs. Pyr], 7.41 (m, 5H, Phe); mass spec m/e 392(M+1); Anal calcd for C$_{25}$H$_{20}$N$_4$O 2HCl 0.5H2O, MW 474.39: C, 63.30; H, 4.89; N, 11.81. Found: C, 63.43; H, 4.69; N, 11.68.

EXAMPLE 2

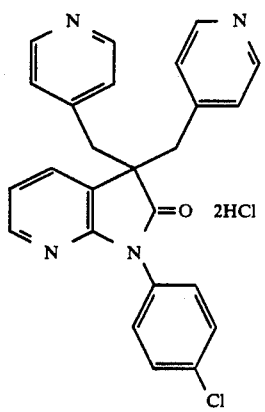

1,3-Dihydro-1-(4-chlorophenyl)-3,3-bis(4-pyridinylmethyl)-2H-Pyrrolo[2,3-b]pyridin-2-one Dihydrochloride By substituting 1-(4-chlorophenyl)-1,3-dihydro-2H-pyrrolo[2,3-b]pyridin-2-one (Ting, et al. EP 0347698A) in Ex 1, the desire product was obtained in 64% yield; mp 137° C. dec.; IR(nujol): 1718 cm$^{-1}$ (CO); $^1$H NMR(DMSOd$_6$ TMS): d [3.70 (d, 2H), 3.93 (d, 2H), CH$_2$—C—CH$_2$], [7.1 (m, 1H), 7.5 (d, 1H), 8.35 (d, 1H), Pyr], [7.65 (d, 2H), 8.77 (2H), 4-Cl-Phe], [8.10 (d, 4H), 8.95 (d, 4H), 2 4-Pyr]; mass spec m/e 427(M+1).

Preparation 2

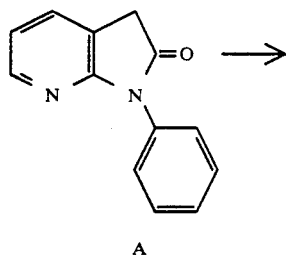

A

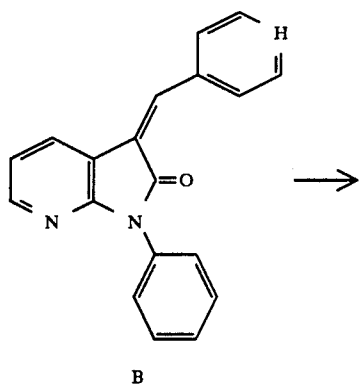

B

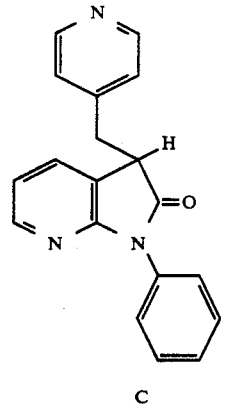

C

A mixture of 1,3-dihydro-1-phenyl-2H-pyrrolo[2,3-b]pyridin-2-one (3.2 g, 15.22 mmol) and pyridine-4-carboxaldehyde (1.63 g, 15.22 mmol) in 50 ml EtOH was treated with triethylamine (1 g) and stirred at room temperature for 16 h. The mixture was diluted with an additional 100 ml EtOH, heated to 80° C., and placed in the cold for 24 h. The resulting solid was collected by filtration, washed with cold EtOH, and dried to give the a,b-unsaturated amide in 99% (4.5 g) yield; mp 199°-200° C.; IR(nujol): 1723 (CO) cm$^{-1}$; $^1$H NMR(CDCl$_3$ TMS): δ[6.88 (m, 1H); 7.71 (d, 1H), 8.16 (d, 1H) 2,3-disubst. Pyr], [7.40 (m, 2H), 7.53 (m, 3H), Phe], [7.48 (d, 2H), 8.76 (d, 2H) 4-Pyr], 7.88 (s, 1H, C═CH); mass spec m/e 300(M+1).

The a,b-unsaturated amide (Prep 2B) (4.0 g, 13.36 mmol) in 100 ml dry THF was treated with NaBH$_4$ (0.51 g, 13.48 mmol) and stirred at room temperature for 16 h. The mixture was refluxed for 1 h, cooled to room temperature, treated with 25 ml acetic acid, and concentrated in vacuo. The residue was partitioned between 150 ml CH$_2$Cl$_2$ and 50 ml saturated NaHCO$_3$, and the organic phase was washed with water and brine, dried over anh. MgSO$_4$, filtered, concentrated in vacuo to give the desired product (Prep 2C) as an homogeneous (TLC, CHCl$_3$-MeOH, 9:1) glass in 94% (3.80 g); IR(CHCl$_3$ film): 1726 (CO) cm$^{-1}$; $^1$H NMR(CDCl$_3$ TMS): d [3.22 (2d, 1H), 3.50 (2d, 1H) CH$_2$-Pyr], 3.96 (m, 1H, CH), [6.93 (dd, 1H), 7.25 (m, 1H), 8.12 (d, 1H), 2,3-disubst. Pyr], 7.0-7.4 (m, 5H, Phe), [7.41 (d, 2H), 8,48 (d, 2H), 4-Pyr]; mass spec m/e 302(M+1).

Preparation 3

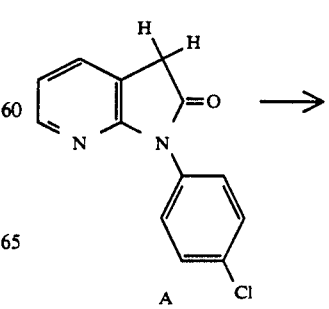

A

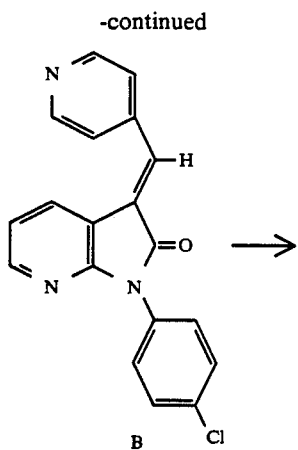

→

1,3-Dihydro-1-(4-chlorophenyl)-3-(3-cyanophenyl)-3-(4-pyridinylmethyl)-2H-Pyrrolo[2,3-b]Pyridin-2-one Dihydrochloride The solution of 1,3-dihydro-1-(4-chlorophenyl)-3-(4-pyridinylmethyl)-2H-pyrrolo[2,3-b]pyridin-2-one (3.0 g, 8.93 mmol) in 75 ml dry THF was treated with NaH (0.26 g, 10.7 mmol) and stirred at room temperature for min. The mixture was then treated dropwise with a solution of a-bromo-m-tolunitrile (1.93 g, 9.82 mmol) dissolved in 25 ml dry THF. The mixture was stirred at room temperature under dry nitrogen for 24 h and concentrated in vacuo. The residue was partitioned between 150 ml $CH_2Cl_2$ and 100 ml water. The organic layer was washed with additional water then brine, dried over anh. $MgSO_4$, filtered, and concentrated to a foam. The foam was dissolved in a minimum amount of MeOH and chromatographed on silica gel using $CHCl_3$—MeOH (95:5) as mobile phase. The appropriate fractions were combined, concentrated in vacuo to 25 ml, and treated with 1N HCl—$Et_2O$ (10 ml). The resulting gummy mixture was concentrated to a foam which was triturated with $Et_2O$, collected by filtration, washed with additional $Et_2O$, and dried to give the desire product in 87% (3.8 g) yield as a foam; IR(nujol): 2229 (CN), 1723 (CO) $cm^{-1}$; $^1H$ NMR(DMSOd$_6$ TMS): d 3.4–3.6(dd, 2H, $CH_2$-Phe), 3.6–3.85 (dd, 2H, $CH_2$-Pyr), [6.91 (d, 2H), 7.25 (m, 3H), 7.61 (m, 3H), Phe-Cl and Phe-CN], [7.37 (dd, 1H), 7.96 (d, 1H), 8.20 (d, 1H), 2,3-Pyr], [7.51 (d, 2H), 8.71 (d, 2H), 1,4-Pyr]; mass spec m/e 451 (M+1). Anal calcd for $C_{27}H_{19}N_4OCl$ HCl, MW 487.39: C, 66.54; H, 4.14; N, 11.50. Found:

1,3-Dihydro-I-(4-chlorophenyl)-3-(4-pyridinylmethyl)-2H-pyrrolo[2,3-b]pyridin-2-one By substituting 1,3-dihydro-1-(4-chlorophenyl)-2H-pyrrolo[2,3-b]pyridin-2-one in Prep 2, the desired intermediate (3C) was prepared in an average yield of mp 177°–179° C. dec.; IR(nujol): 1732 $cm^{-1}$ (CO); $^1H$ NMR(CDCl$_3$ TMS): d [3.41 (m, 1H), 3.52 (m, 1H), $CH_2$-Pyr], 4.03 (t, 1H, CH-C-Pyr), [7.02 (m, 1H), 7.3 (M, 1H), 8.18 (d, 1H) 2,3-Pyr], 7.35 (m, 4H, Phe-Cl), 7.35, 8.46 (2d, H, 4-Pyr); mass spec m/e 336(M+1).

EXAMPLE 3

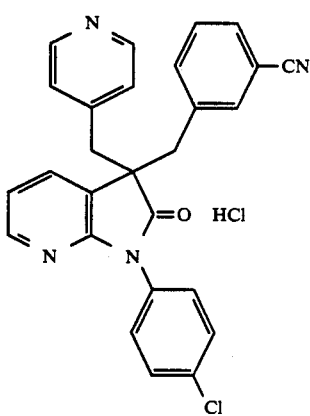

EXAMPLE 4

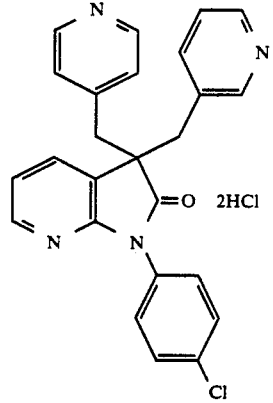

1,3-Dihydro-1-(4-chlorophenyl)-3-(3-pyridinylmethyl)-3-(4-pyridinylmethyl)-2H-pyrrolo[2,3-b]pyridin-2-one Dihydrochloride A mixture of 1,3-dihydro-1-(4-chlorophenyl)-3-(4-pyridinylmethyl)-2H-pyrrolo[2,3-b]pyridin-2-one (3.0 g, 8.93 mmol) and 20 ml 1N NaOH was treated with enough MeOH to effect solution. The mixture was treated dropwise with 3-picolyl chloride hydrochloride (1.6 g, 9.82 mmol) in 10 ml water. The mixture was stirred at room temperature for 2 h, and treated with an additional 20 ml 1N NaOH. The mixture was stirred at room temperature for 24 h and concentrated in vacuo. The residue was partitioned between 200 ml $CH_2Cl_2$, washed with brine, dried over $MgSO_4$, filtered, and treated with 20 ml 1N HCl/Et$_2$O. The resulting precipitate was collected by filtration, washed with ether, and dried to give the desired product in 90% (4.0 g) yield; mp 208°–211° C., dec.; IR(nujol): 1720 cm$^{-1}$ (CO); $^1$H NMR(DMSOd$_6$ TMS): d 3.65 [m, 2H, CH$_2$-(3-Pyr)], 3.71–3.91 [q, 2H, CH$_2$-(4-Pyr)], [7.06 (d, 2H), 7.22 (m, 1H), 7.53 (d, 2H), 7.60 (d, 2H), 7.85 (dd, 1H), 8.04 (dd, 2H), 8.22 (d, 1H), 8.52 (s, 1H), 8.84 (d, 3H), Ar]; mass spec m/e 427 (M+1).

EXAMPLE 5

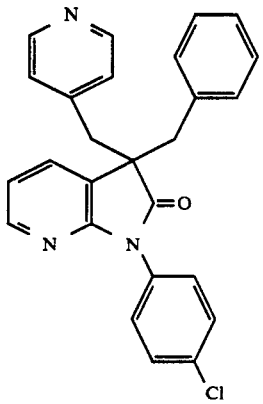

1,3-Dihydro-1-(4-chlorophenyl)-3-(phenylmethyl)-3-(4-pyridinylmethyl)-2H-pyrrolo[2,3-b]pyridin-2-one A mixture of 1,3-dihydro-1-(4-chlorophenyl)-3-(4-pyridinylmethyl)-2H-pyrrolo[2,3-b]pyridin-2-one (3.0 g, 8.93 mmol) and 20 ml 1N NaOH was treated with enough MeOH to effect solution. The mixture was treated with benzyl chloride (1.24 g, 9.82 mmol) and stirred at room temperature for 24 h. The resulting solid was collected by filtration, washed with water, and dried in vacuo to give the desired product in 87% (3.30 g) yield; mp 182°–185° C.; IR(nujol): 1727 cm$^{-1}$ (CO); $^1$H NMR(CDCl$_3$ TMS): d 3.29 (dd, 2H, Phe-CH$_2$), 3.4–3.–7 (g, 2H, Pyr-CH$_2$), [6.75 (d, J=8.8, 2H), 6.9 (m, 2H), 7.1 (m, 6H), 7.35 (d, J=8.4, 2H), 7.61 (d, J=7.3, 1H), 8.05 (d, J=6.6, 1H), 8.33 (d, J=6.2, 2H), Ar]; mass spec m/e 426(M+1). Anal calcd for C$_{26}$H$_{20}$N$_3$OCl, MW 425.92: C, 73.32; H, 4.73; N, 9.87. Found: C, 73.61; H, 4.93; N, 9.83.

EXAMPLE 6

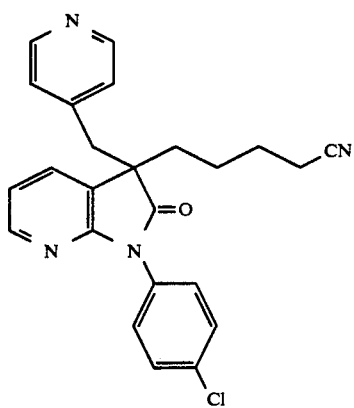

1,3-Dihydro-1-(4-chlorophenyl)-3-(4-pyridinylmethyl)-2H-pyrrolo[2,3-b]pyridin-2-one-3-pentanenitrile A solution of 1,3-dihydro-1-(4-chlorophenyl)-3-(4-pyridinylmethyl)-2H-pyrrolo[2,3-b]pyridin-2-one (3.0 g, 8.93 mmol) in 100 ml dry THF was treated with NaH (0.26 g, 10.72 mmol), stirred at room temperature for 30 min, and treated with 5-bromovalero-nitrile (1.6 g, 9.87 mmol) in 25 ml dry THF. The mixture was stirred at room temperature under dry nitrogen for 24 h, and concentrated in vacuo. A portion of the residue was subjected to preparative HPLC to give the desired product as a slightly yellow oil; IR(nujol): 2246(CN), 1728(CO) cm$^{-1}$; $^1$H NMR(CDCl$_3$ TMS): d 1.26 (m, 2H, CH$_2$—CC—CN), 1.65 (m, 2H, CH$_2$—C—CN), 2.06, 2.24 (2m, 2H, CH$_2$—CCC—CN), 2.31 (t, 2H, CH$_2$—CN), [3.17 (d, J=12.8), 3.41 (d, J=12.8) CH$_2$-Pyr], [6.98 (d, J=6.4, 2H), 8.32 (d, J=6.4) 4-Pyr], [7.07 (d, J=8.6, 2H), 7.44 (d, J=8.6, 2H) 4-Cl-Phe], 7.13, 7.62, 8.18 (3m, 3H, Pyr); mass spec m/e 417(M+1).

EXAMPLE 7

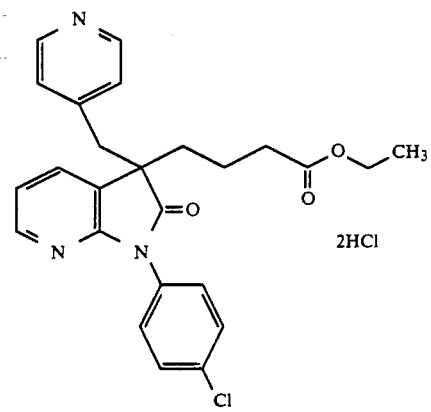

1,3-Dihydro-1-(4-chlorophenyl)-3-(4-pyridinylmethyl)-2H-pyrrolo[2,3-b]pyridin-2-one-3-butanoic acid ethyl ester Hydrochloride By substituting ethyl 4-bromobutyrate in Ex 6, the desire product was obtained as a foam in 22% yield after column chromatography: $^1$H NMR (300 MHz, CDCl$_3$ TMS) δ 1.24 (t, 3H, CH$_3$), 1.4 (m, 2H, CH$_2$—C—CO), 2.0–2.35 (m, H, CH$_2$—C—CH$_2$—CO), [3.07, (d, J=12.5, 1H), 3.29 (d, J=2.5, 1H, CH$_2$-Pyr], 4.11 (q, 2H, OCH$_2$), [6.76 (d, J=6, 2H), 8.31 (d, J=6, 2H) 4-Pyr], [7.04 (d, J=8.8, 2H), 7.40 (d, J=8.8, 2H) 4-Cl-Phe], [7.1 (m, 1H), 7.6 (m, 1H), 8.1 (m, 1H) 2,3-Pyr]); IR (Nujol) 1723 (C=O) cm$^{-1}$; MS (NH$_3$-CI) m/e 450(M+1)/100; anal calcd for C$_{25}$H$_{24}$N$_3$O$_3$Cl 2HCl, MW 522.86: C, 57.43; H, 5.01; N, 8.01; found: C, 57.69; H, 4.86; N, 7.86.

EXAMPLE 8

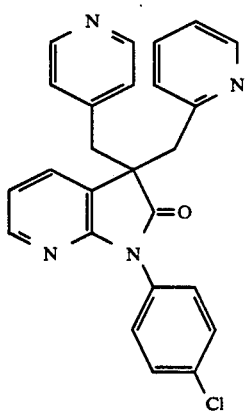

1,3-Dihydro-1-(4-chlorophenyl)-3-(2-pyridinylmethyl)-3-(4-pyridinylmethyl)-2H-pyrrolo[2,3-b]pyridin-2-one A suspension of 1,3-dihydro-1-(4-chlorophenyl)-3-(4-pyridinylmethyl)-2H-pyrrolo[2,3-b]pyridin-2-one (3.0 g, 8.93 mmol) in 20 ml 1N NaOH was treated with enough MeOH to effect solution. The solution was treated dropwise with a solution of 2-picolylchloride hydrochloride (1.6 g, 9.82 mmol) in 10 ml water over 10 min. The mixture was stirred at room temperature for 16 h, and the resulting solid was colledted by filtration, washed with water, and dried. The solid was recrystallized from CHCl$_3$—C$_6$H$_{12}$ to give the desired product in 79% (3.0 g) yield : m.p. 193°–195° ; $^1$H NMR (300 MHz, CDCl$_3$ TMS) δ [3.34 (d, J=12, 1H), 3.56 (d, J=12, 1H) CH$_2$-(2-Pyr)], [3.48 (d, J=14, 1H), 3.78 (d, J=14, 1H) CH$_2$-(4-Pyr)], [6.95 (m, 1H), 8.0 (m, 1H), 8.27 (d, J=7, 1H) Pyr], [7.0 (m, 6H), 7.5 (m, 2H) 2-Pyr & 4-Cl-Phe]), [7.42 (d, J=7, 2H), 8.32 (d, J=7, 2H) 4-Pyr]; IR (Nujol) 1732 (C═O) cm$^{-1}$; MS (NH$_3$-CI) m/e 427(M+1)/100; Analysis calc'd for C$_{25}$H$_{19}$N$_4$OCl H$_2$O: C, 67.49; H, 4.76; N, 12.59; found: C, 67.38; H, 5.01; N, 12.34.

EXAMPLE 9

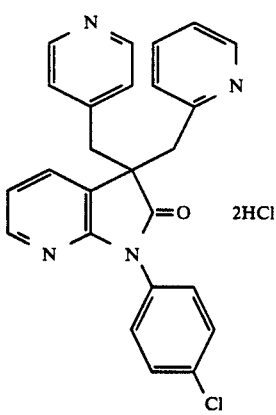

1,3-Dihydro-1-(4-chlorophenyl)-3-(2-pyridinylmethyl)-3-(4-pyridinylmethyl)-2H-pyrrolo[2,3-b]pyridin-2-one Dihydrochloride A solution of the free base (Ex. 8) in CHCl$_3$ was treated with excess HCl/Et$_2$O, and the resulting white fluffy solid was collected by filtration, washed with Et$_2$O, and dried in vacuo to give the desired salt in quantitative yield: m.p. 170°–175° C. dec.; $^1$H NMR (300 MHz, DMSOd$_6$ TMS) δ [3.62 (d, J=12.5, 1H), 3.79 (d, J=12.5, 1H), CH$_2$-Pyr], 3.78 (s, 2H, CH$_2$-Pyr), [7.06 (m, 1H), 7.85 (m, 1H), 8.36 (m, 1H), Pyr], [7.22 (d, J=8.8, 2H), 7.57 (m, 4H), 8.72 (d, J=6.2), 4-Phe & 4-Pyr]), [7.31 (d, J=7.3, 1H), 7.57 (m, 1H), 7.94 (d, J=4.0, 1H), 7.96 (d, J=3.3, 1H), 2-Pyr]); IR (nujol) 1718 (C═O) cm$^{-1}$; MS (NH$_3$—CI) m/e 427(M+1).

EXAMPLE 72

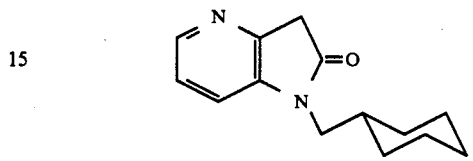

N-Cyclohexanemethyl-4-azoxindole

A modification of the procedure described by Goehring, Wolfe, et al. , J. Am. Chem. Soc., 1985, 107(2), 435–443. A solution of 2-chloro-(N-cyclohexanemethylacetamido)pyridine (2.4 g, 9.0 mmol) in 200 ml dry THF was treated with LDA (3.86 g, 36.0 mmol) and stirred at room temperature for 5 min under dry nitrogen. The resulting reddish solution was transferred to quartz photochemical reaction flask and subjected to uv light generated by a Hanovia lamp #679A36 for 4 h. The mixture was treated with 150 ml sat. NH$_4$Cl, and the organic layer was separated, dried over MgSO$_4$, filtered, and concentrated in vacuo to a brown gum in a yield of 92% (1.90 g): IR (nujol): 1722 (C═O) cm$^{-1}$; MS (NH3-CI) m/e 231(M+1)/100%; mass spec showed no starting material or des-Cl product of the starting material (M+1=233).; The material was used without further purification or characterization.

EXAMPLE 72

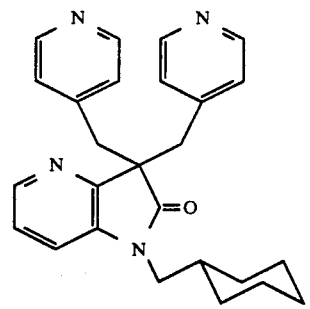

1,3-Dihydro-1-cyclohexanemethyl-3,3-bis(4-pyridinylmethyl)-2H-pyrrolo[2,3-b]pyridin-2-one A mixture of N-cyclohexanemethyl-4-azoxindole (1.5 g, 6.5 mmol) and 1N NaOH (32.5 ml) was treated with enough MeOH to effect solution. The mixture was stirred at room temperature and treated dropwise over one hour with a solution of 4-picolylchloride hydrochloride (2.3 g, 14.0 mmol) in 25 ml water. The mixture was stirred at room temperature for 24 h and concentrated in vacuo. The residue was triturated with water, and the aqueous phase was discarded. The crude product was column chromatographed on silica gel using CH$_2$Cl$_2$ as mobile phase, and appropriate fractions were combined and concentrated to give the desired product as an amorphous brownish solid in 25% yield; tlc homogenous (CHCl$_3$—MeOH, 9:1), m/e 413(M+1).

BIOCHEMICAL TEST PROCEDURE

Neurotransmitter release assay

The neurotransmitter release activity of the compounds of this invention were determined as reported by Nickolson, et al, (1990) Drug Development Research, 19, 285–300 of a modification of the procedure described by Mulder, et al., Brain Res., 1974, 70, 372.

Male Wistar rats (Charles River) weighing 175–200 grams were used. The rats were housed for at least seven days before the experiment in animal facility under 12/12 hour light/dark cycle. Deionized water and standard rat chow (Purina) were available ad labium.

Rats were decapitated and brains were dissected immediately. Slices (0.3 mm thick) from the parietal cortex were prepared manually using a recessed Lucite guide and subsequently cut into 0.25×0.25 mm squares.

Slices (approximately 100 mg wet weight) were incubated in 10 ml Krebs-Ringer medium (KR) containing NaCl (116 mM), KCl (3 mM), CaCl$_2$ (1.3 mM), MgCl$_2$ (1.2 mM), KH$_2$PO$_4$ (1.2 mM), Na$_2$SO$_4$ (1.2 mM), NaHCO$_3$ (25.0 mM), and glucose (11.0 mM), to which was added 10 uCi $^3$H-choline (specific activity approximately 35 Ci/mM; NEN) and 10 mM unlabeled choline to give a final concentration of one micromole. The brain preparations were incubated for 30 min at 37° C. under a steady flow of 95% O$_2$/5% CO$_2$. Under these conditions, part of the radioactive choline taken up by the preparation was converted into radioactive acetylcholine (ACh) by the cholinergic nerve endings stored in synaptic vesicles, and released upon depolarization by high potassium ion (K+) containing media.

After labelling of the ACh stores, the slices were washed three times with non-radioactive KR medium and transferred to a superfusion apparatus to measure the drug effects on ACh release. The superfusion apparatus consisted of 10 thermostated glass columns of 5 mm diameter which were provided with GF/F glass fiber filters to support the slices (approximately 10 mg tissue/column). Superfusion was carried out in KR-medium (0.3 ml/min) containing 10 mM hemicholine-3 (HC-3). The HC-3 prevents the reuptake of choline formed during the superfusion from phospholipids and released ACh, which would be converted into unlabeled ACh and released in preference to the pre-formed labelled ACh. The medium was delivered by a 25-channel peristaltic pump (Ismatec by Brinkman) and warmed to 37° C. in a thermostated stainless steel coil before entering the superfusion column. Each column was provided with a 4-way slider valve (Beckmann Instruments) which allowed rapid change of low to high K+/KR-medium, and with two 10-channel 3-way valves that were used to change from drug-free to drug-containing low and high K+/KR-medium.

After 15 min of washout of non-specifically bound radioactivity, collection of 4 min fractions was initiated. After three 4 min collections, the original medium was changed to a KR-medium in which the KCl concentration had been increased to 25 mM (high K+ medium) (S1). Depolarization-induced stimulation of release by high K+/KR-medium lasted for 4 min. Drug free low and high K+/KR-media were then substituted by drug- and vehicle-containing low- and high-K+/KR-medium, and superfusion was continued for three 4 min collections with low K+/KR-medium, one 4 min collection with high K+/KR-medium (S2), and two 4 min collections with low K+/KR-medium.

Drug was added to the media by 100-fold dilutions of appropriate concentrations of the drug (in 0.9% saline) with either low- or high-K+/KR-medium.

All superfusion fractions were collected in liquid scintillation counting vials. After superfusion, the slices were removed from the superfusion columns and extracted with 1.0 ml of 0.1 N HCl. Liquiscint (NEN) counting fluid (12 ml) was added to superfusion fractions and extracts, and the samples were counted in a Packard Tricarb Liquid Scintillation Counter. No corrections were made for quenching.

The ratio of S2/S1 (as compared to controls where no drug was present during S2) was a measure of the ability of the drug to enhance or depress stimulus-induced acetylcholine release.

TABLE I
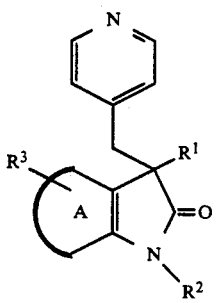
| Cmpd | Core | R¹ | % Yield | mp, °C. | % ACh Rel @ 10 mM |
|---|---|---|---|---|---|
| 1 | 7-azaindolin-2-one, N-phenyl | 4-Pyr—CH₂ HCl 0.5 H₂O | 27 | 184–185 | 423 |
| 2 | 7-azaindolin-2-one, N-(4-chlorophenyl) | 4-Pyr—CH₂ HCl | 64 | 137 dec. | 626 |
| 3 | 7-azaindolin-2-one, N-(4-chlorophenyl) | 3-CN—Phe—CH₂ | 87 | foam | 537 |
| 4 | 7-azaindolin-2-one, N-(4-chlorophenyl) | 3-Pyr—CH₂ HCl | 90 | 209–211 dec. | 299 |
| 5 | 7-azaindolin-2-one, N-(4-chlorophenyl) | Phe—CH₂ | 87 | 182–185 | 257 |

TABLE I-continued

| Cmpd | Core | R¹ | % Yield | mp, °C. | % ACh Rel @ 10 mM |
|---|---|---|---|---|---|
| 6 | | (CH$_2$)$_4$—CN | isolated by prep HPLC | oil | |
| 7 | | (CH$_2$)$_3$—CO$_2$Et | 22 | foam | |
| 8 | | 2-Pyr—CH$_2$ | 79 | 193–194 | |
| 9 | | 2-Pyr—CH$_2$ 2 HCl | 100 | 175 dec | |
| 10 | | 4-Pyr—CH$_2$ | | | |

TABLE I-continued
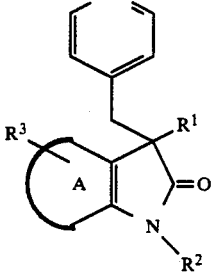
| Cmpd | Core | R¹ | % Yield | mp, °C. | % ACh Rel @ 10 mM |
|---|---|---|---|---|---|
| 11 | 7-azaindolin-2-one with N-(4-chlorophenyl) | 3-tetrahydrofuryl-CH | | | |
| 12 | 6-azaindolin-2-one, N-Ph | 4-Pyr—CH₂ | | | |
| 13 | 6-azaindolin-2-one, N-Ph | 4-Pym—CH₂ | | | |
| 14 | 5-azaindolin-2-one, N-Ph | 4-Pyr—CH₂ | | | |
| 15 | pyrrolo[2,3-d]pyrimidin-2-one, N-Ph | 4-Pyr—CH₂ | | | |
| 16 | pyrrolo-pyrazine core, N-Ph | 4-Pyr—CH₂ | | | |
| 17 | pyrrolo-pyrazine core, N-Ph | 4-Pyr—CH₂ | | | |

TABLE I-continued

[Core structure: bicyclic system with pyridin-4-ylmethyl group at R¹ position, R² on nitrogen, R³ on ring A, with C=O]

| Cmpd | Core | R¹ | % Yield | mp, °C. | % ACh Rel @ 10 mM |
|------|------|-----|---------|---------|-------------------|
| 18 | pyrrolo-pyridazinone, N-Ph | 4-Pyr—CH₂ | | | |
| 19 | cyclopenta-pyridazinone, Ph | 4-Pyr—CH₂ | | | |
| 20 | pyrrolo-pyrrolone, N-Me, N-Ph | 4-Pyr—CH₂ | | | |
| 21 | pyrrolo-pyrrolone, N-Ph | 4-Pyr—CH₂ | | | |
| 22 | furo-pyrrolone, N-Ph | 4-Pyr—CH₂ | | | |
| 23 | furo-pyrrolone, N-Ph | 4-Pyr—CH₂ | | | |
| 24 | thieno-pyrrolone, N-Ph | 4-Pyr—CH₂ | | | |
| 25 | thieno-pyrrolone, N-Ph | 4-Pyr—CH₂ | | | |

TABLE I-continued

| Cmpd | Core | R[1] | % Yield | mp, °C. | % ACh Rel @ 10 mM |
|---|---|---|---|---|---|
| 26 | (N, NH, N, Ph core) | 4-Pyr—CH$_2$ | | | |
| 27 | (N, N, N, Ph core) | 4-Pyr—CH$_2$ | | | |
| 28 | (Me-N, N, Ph core) | 4-Pyr—CH$_2$ | | | |
| 29 | (N, S, Ph core) | 4-Pyr—CH$_2$ | | | |
| 30 | (S, N, Ph core) | 4-Pyr—CH$_2$ | | | |
| 31 | (N, O, Ph core) | 4-Pyr—CH$_2$ | | | |
| 32 | (O, N, Ph core) | 4-Pyr—CH$_2$ | | | |

TABLE I-continued

[Structure: bicyclic lactam with pyridin-4-ylmethyl group at position bearing R¹, ring A with R³ substituent, N-R² lactam]

| Cmpd | Core | R¹ | % Yield | mp, °C. | % ACh Rel @ 10 mM |
|------|------|-----|---------|---------|-------------------|
| 33 | 7-azaindolin-2-one, N-Ph | (CH₂)₂—CO₂Et | | | |
| 34 | 7-azaindolin-2-one, N-Ph | (CH₂)₃—CO₂Et | | | |
| 35 | 7-azaindolin-2-one, N-Ph | (CH₂)₃—CO₂Et | | | |
| 36 | 7-azaindolin-2-one, N-Ph | (CH₂)₃—CN | | | |
| 37 | 7-azaindolin-2-one, N-Ph | (CH₂)₄—CN | | | |
| 38 | 7-azaindolin-2-one, N-Ph | (CH₂)₅—CN | | | |
| 39 | 7-azaindolin-2-one, N-Ph | (CH₂)₃—CO₂Me | | | |
| 40 | 7-azaindolin-2-one, N-Ph | (CH₂)₃—CO₂(n-Pr) | | | |

TABLE I-continued
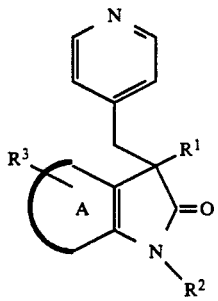
| Cmpd | Core | R¹ | % Yield | mp, °C. | % ACh Rel @ 10 mM |
|---|---|---|---|---|---|
| 41 | 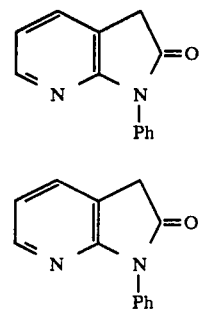 | $(CH_2)_3-CO_2(i\text{-}Pr)$ | | | |
| 42 | 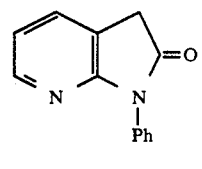 | $(CH_2)_3-CO_2(n\text{-}Bu)$ | | | |
| 43 | 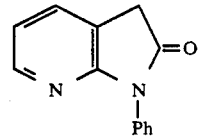 | $(CH_2)_3-CO_2(t\text{-}Bu)$ | | | |
| 44 | 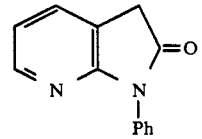 | $(CH_2)_3-CO_2C_6H_{11}$ | | | |
| 45 | 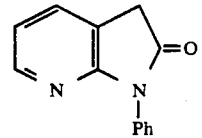 | $(CH_2)_3-CO_2CH_2C_6H_5$ | | | |
| 46 | 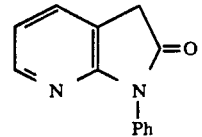 | $(CH_2)_3-CO_2H$ | | | |
| 47 | 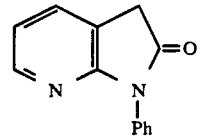 | $(CH_2)_3-SO_2NH_2$ | | | |
| 48 | 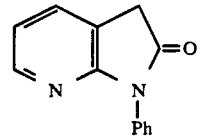 | $(CH_2)_3-SO_2NMe_2$ | | | |

TABLE I-continued

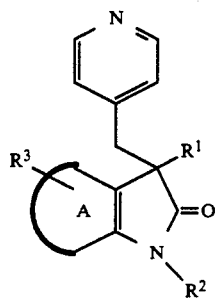

| Cmpd | Core | R¹ | % Yield | mp, °C. | % ACh Rel @ 10 mM |
|---|---|---|---|---|---|
| 49 | (pyridine fused pyrrolinone, N-Ph) | (CH₂)₃—OAc | | | |
| 50 | (pyridine fused pyrrolinone, N-CH₂C₆H₅) | 4-Pyr—CH₂ | | | |
| 51 | (pyridine fused pyrrolinone, N-CH₂C₆H₁₁) | 4-Pyr—CH₂ | | | |
| 52 | (pyridine fused pyrrolinone, N-CH₂C₅H₉) | 4-Pyr—CH₂ | | | |
| 53 | (pyridine fused pyrrolinone, N-CH₂(CH₂)₄Me) | 4-Pyr—CH₂ | | | |
| 54 | (pyridine fused pyrrolinone, N-CH₂—(4-P)) | 4-Pyr—CH₂ | | | |
| 55 | (pyridine fused pyrrolinone, N-CH₂—(3-Cl—)) | 4-Pyr—CH₂ | | | |
| 56 | (5-Cl pyridine fused pyrrolinone, N-Ph) | 4-Pyr—CH₂ | | | |

TABLE I-continued
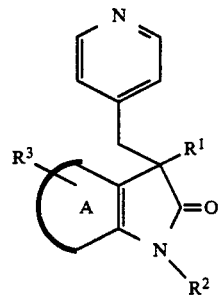
| Cmpd | Core | R[1] | % Yield | mp, °C. | % ACh Rel @ 10 mM |
|---|---|---|---|---|---|
| 57 | F, Ph (core) | 4-Pyr—CH$_2$ | | | |
| 58 | Br, Ph (core) | | | | |
| 59 | Me, Ph (core) | 4-Pyr—CH$_2$ | | | |
| 60 | F$_3$C, Ph (core) | 4-Pyr—CH$_2$ | | | |
| 61 | Me$_2$N, Ph (core) | 4-Pyr—CH$_2$ | | | |
| 62 | MeO, Ph (core) | 4-Pyr—CH$_2$ | | | |
| 63 | AcO, Ph (core) | 4-Pyr—CH$_2$ | | | |

TABLE I-continued

| Cmpd | Core | R¹ | % Yield | mp, °C. | % ACh Rel @ 10 mM |
|---|---|---|---|---|---|
| 64 | Me-C(O)- substituted pyridine fused pyrrolinone, N-Ph | 4-Pyr—CH₂ | | | |
| 65 | MeSO₂- substituted pyridine fused pyrrolinone, N-Ph | 4-Pyr—CH₂ | | | |
| 66 | Cl- substituted pyridine fused pyrrolinone, N-Ph | 4-Pyr—CH₂ | | | |
| 67 | O₂N- substituted pyridine fused pyrrolinone, N-Ph | 4-Pyr—CH₂ | | | |
| 68 | MeO- substituted pyridine fused pyrrolinone, N-Ph | 4-Pyr—CH₂ | | | |
| 69 | HO- substituted pyridine fused pyrrolinone, N-Ph | 4-Pyr—CH₂ | | | |
| 70 | NC- substituted pyridine fused pyrrolinone, N-Ph | 4-Pyr—CH₂ | | | |

TABLE I-continued

| Cmpd | Core | R¹ | % Yield | mp, °C. | % ACh Rel @ 10 mM |
|---|---|---|---|---|---|
| 71 | | 4-Pyr—CH₂ | | | |
| 72 | | 4-Pyr—CH₂ | 25 | amorphous | >150 |

BEHAVIORAL TEST PROCEDURE

Rat Passive Avoidance (PA) Hypoxia Induced Amnesia: Unfasted male CD rats, weighing between 165–210 g were trained in a PA apparatus using the following procedure: rats were placed in the clear side of the two compartment chamber and allowed 90 seconds to enter the dark compartment. Ten seconds after entering the dark chamber, a 3 second foot shock (1.0 mA) was applied to the grid floor followed by an additional 10 second delay, and another 3 second foot shock was applied. Retentions were tested 4 hours later. The rats were allowed 300 seconds to enter the dark compartment; time was taken. Memory disruption was induced by exposing the rats to a gas mixture containing 6.5% oxygen supplemented with nitrogen for 30 minutes prior to passive avoidance training. Doses of the test compound were administered (0.1 ml/100 g s.c.) relative to time of PA training. Using this method, Example 1 was shown to have the following latency as compared to control:

Example 1 ED$_{150}$, s.c.=1.3 mg/kg

UTILITY

The foregoing test results suggest that the compounds of this invention have utility in the treatment of cognitive disorders and/or neurological function deficits and/or mood and mental disturbances in patients suffering from nervous system disorders like Alzheimer's disease, Parkinson's disease, senile-dementia, multi-infarct dementia, Huntington's disease, mental retardation, Myasthenia Gravis, etc. Compounds of this invention can be administered to treat said deficiencies by any means that produces contact of the active agent with the agent's site of action in the body of a mammal. The compounds can be administered by any conventional means available for use in conjunction with pharmaceuticals either as individual therapeutic agent or in combination of therapeutic agents. They can be administered alone, but are generally administered with a pharmaceutical carrier selected on the basis of the chosen route of administration and standard pharmaceutical practice.

The dosage administered will vary depending on the use and known factors such as the pharmacodynamic character of the particular agent, and its mode and route of administration; the recipient's age, weight, and health; nature and extent of symptoms; kind of concurrent treatment; frequency of treatment; and the desired effect. For use in the treatment of said diseases or conditions, the compounds of this invention can be orally administered daily at a dosage of the active ingredient of 0.001 to 100 mg/kg of body weight. Ordinarily, a dose of 0.01 to 10 mg/kg/day in divided doses one to four times a day, or in sustained release formulation was effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally in solid dosage forms, such as capsules, tablets, and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar coated or film coated to mask any unpleasant taste, or used to protect the active ingredients from the atmosphere, or to allow selective disintegration of the tablet in the gastrointestinal tract.

Liquid dosage forms for oral administration can contain coloring and flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in this field.

Useful pharmaceutical dosage-forms for administration of the compounds of this invention can be illustrated as follows:

Capsules

A large number of unit capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil was prepared and injected by means of a positive displacement was pumped into gelatin to form soft gelatin capsules containing 100 mg of the active ingredient. The capsules are washed and dried.

Tablets

A large number of tablets are prepared by conventional procedures so that the dosage unit was 100 mg of active ingredient, 0.2 mg of collodial silicon dioxide, 5 mg of magnesium stearate, 275 mg of microcrystalline cellulose, 11 mg of starch, and 98.8 mg lactose. Appropriate coatings may be applied to increase palatability or delayed absorption.

What is claimed is:

1. A compound of the Formula I

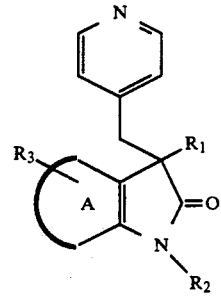

Formula I or a pharmaceutically acceptable salt thereof wherein A is a heteroaromatic system selected from the group consisting of

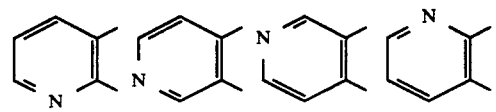

and wherein:
$R^1$ is $(CH_2)m\text{-}W$ or $(CH_2)n\text{-}R^4$;
$R^2$ is alkyl of 1–7 carbons, benzyl substituted with 0–3 $R^4$, or phenyl substituted with 0–3 $R^5$;
$R^3$ is H, alkyl of 1–6 carbons, halogen, CN, $OR^2$, $N(R^7R^8)$, $S(O)pR^7$, $NO_2$, or $CF_3$;
$R^4$ is $CO_2R^7$, $CON(R^7R^8)$ CN, $OR^2$, $N(R^7R^8)$, $S(O)pR^7$, F, Cl, Br, $NO_2$, or $COR^7$;
$R^5$ is $CO_2R^7$, $CON(R^7R^8)$, CN, $OR^7$, $N(R^7R^8)$, $S(O)pR^7$, F, Cl, Br, $NO_2$, $COR^7$, or $CF_3$;
$R^7$ and $R^8$ independently are H, or alkyl of 1–6 carbons;
W is pyridyl, pyrimidinyl, pyrazinyl, pyridazinyl, pyrazolyl, tetrahydrofuranyl, thienyl, or phenyl optionally substituted with 0–2 $R^5$;
m is 1 to 4;
n is 1 to 6; and
p is 0 to 2.

2. A compound of claim 1 wherein:
A is

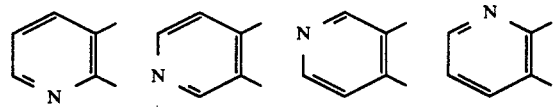

$R^1$ is $(CH_2)m\text{-}W$ or $(CH_2)n\text{-}R^4$;
$R^2$ is alkyl of 1–7 carbon atoms, benzyl substituted with 0–3 $R^4$, or phenyl substituted with 0–3 $R^5$;
$R^3$ is H, alkyl of 1–6 carbon atoms, halogen, CN, $OR^7$, $N(R^7R^8)$, $S(O)pR^7$, $NO_2$, or $CF_3$;
$R^4$ is $CO_2R^7$, $CON(R^7R^8)$, CN, $OR^7$, $N(R^7R^8)$, $S(O)pR^7$, F, Cl, Br, $NO_2$, or $COR^7$;
$R^5$ is $CO_2R^7$, $CON(R^7R^8)$, CN, $OR^7$, $N(R^7R^8)$, $S(O)pR^7$, F, Cl, Br, $NO_2$, $COR^7$, or $CF_3$;
$R^7$ and $R^8$ independently are H, or alkyl of 1–6 carbon atoms;
W is pyridinyl, pyrimidinyl, pyrazinyl, pyridazinyl, pyrazolyl, tetrahydrofuranyl, thienyl, or phenyl optionally substituted with 0–2 $R^5$;
m is 1 to 4;
n is 1 to 6; and
p is 0 to 2.

3. A compound of claim 2 wherein

A is

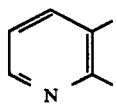

$R^1$ is $(CH_2)m$-W or $(CH_2)n$-$R^4$;

$R^2$ is alkyl of 1–7 carbon atoms, benzyl substituted with 0–3 $R^4$, or phenyl substituted with 0–3 $R^5$;

$R^3$ is H, alkyl of 1–4 carbons, halogen, CN, $OR^7$, $N(R^7R^8)$, $S(O)pR^7$, $NO_2$, or $CF_3$;

$R^4$ is $CO_2R^7$, $CON(R^7R^8)$, CN, $S(O)pR^7$, or $COR^7$;

$R^5$ is $CO_2R^7$, $CON(R^7R^8)$, CN, $OR^7$, $N(R^7R^8)$, $S(O)pR^7$, F, Cl, Br, NO, $COR^7$, or $CF_3$;

$R^7$ and $R^8$ independently are H, or alkyl or 1–6 carbons;

W is pyridyl, pyrimidinyl, tetrahydrofuranyl;

m is 1 to 4;

n is 1 to 6; and p is 1 or 2.

4. A compound of claim 3 wherein $R^1$ is 2,3 or 4-pyridyl-$CH_2$-,4-pyrimidinyl-$CH_2$-,3-CN phenyl-$CH_2$-,phenyl-$CH_2$—, —$(CH_2)4$ CN, or —$(CH_2)3CO_2$ Et;

$R^2$ is phenyl; and $R^3$ is H or Cl.

5. A compound of claim 4 wherein $R^1$ is 3 or 4-pyridyl-$CH_2$—, 3—CN phenyl-$CH_2$ or phenyl-$CH_2$.

6. The compound of claim 1 which is 1,3-Dihydro-1-phenyl-3,3-bis(4-pyridinylmethyl)-2H-pyrrolo[2,3-b]pyridin-2-one Dihydrochloride.

7. The compound of claim 1 which is 1,3-Dihydro-1-(4-chlorophenyl)-3,3-bis(4-pyridinylmethyl)-2H-pyrrolo 2,3-b]pyridin-2-one Dihydrochloride.

8. The compound of claim 1 which is 1,3-Dihydro-1-(4-chlorophenyl)-3-(3-cyanophenyl)-3-(4-pyridinylmethyl)-2H-pyrrolo[2,3-b]pyridin-2-one Dihydrochloride.

9. The compound of claim 1 which is 1,3-Dihydro-1-(4-chlorophenyl)-3-(3-pyridinylmethyl)-3-(4-pyridinylmethyl)-2H-pyrrolo[2,3-b]pyridin-2-one Dihydrochloride.

10. The compound of claim 1 which is 1,3-Dihydro-1-(4-chlorophenyl)-3-(phenylmethyl)-3-(4-pyridinylmethyl)-2H-pyrrolo[2,3-b]pyridin-2-one.

11. A pharmaceutically composition comprising an amount of a compound of claim 1 effective to treat cognitive disorders and a pharmaceutically acceptable carrier.

12. A pharmaceutical composition as recited in claim 11 wherein the compound is of the formula

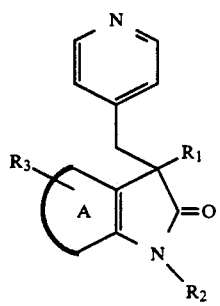

Formula I or a pharmaceutically acceptable salt thereof, wherein

A is

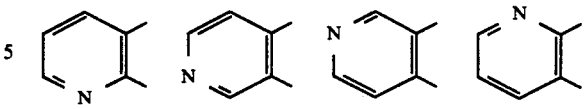

$R^1$ is $(CH_2)m$-W or $(CH_2)n$-$R^4$;

$R^2$ is alkyl of 1–7 carbon atoms, benzyl substituted with 0–3 $R^4$, or phenyl substituted with 0–3 $R^5$;

$R^3$ is H, alkyl of 1–6 carbon atoms, halogen, CN, $OR^7$, $N(R^7R^8)$, $S(O)pR^7$, $NO_2$, or $CF_3$;

$R^4$ is $CO_2R^7$, $CON(R^7R^8)$, CN, $OR^7$, $N(R^7R^8)$, $S(O)pR^7$, F, Cl, Br, $NO_2$, or $COR^7$;

$R^5$ is $CO_2R^7$, $CON(R^7R^8)$, CN, $OR^7$, $N(R^7R^8)$, $S(O)pR^7$, F, Cl, Br, $NO_2$, $COR^7$, or $CF_3$;

$R^7$ and $R^8$ independently are H, alkyl of 1–6 carbon atoms;

W is pyridyl, pyrimidinyl, pyrazinyl, pyridazinyl, pyrazolyl, tetrahydrofuranyl, thienyl, or phenyl optionally substituted with 0–2 $R^5$;

m is 1 to 4;

n is 1 to 6; and p is 0 to 2.

13. A pharmaceutical composition as recited in claim 12 wherein the compound is of the formula

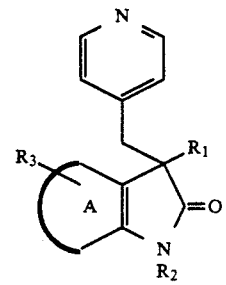

Formula I or a pharmaceutically acceptable salt thereof, wherein

A is

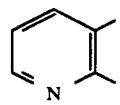

$R^1$ is $(CH_2)m$-W or $(CH_2)n$-$R^4$;

$R^2$ is alkyl of 1–7 carbon atoms, benzyl substituted with 0–3 $R^4$, or phenyl substituted with 0–3 $R^5$;

$R^3$ is H, alkyl of 1–4 carbons, halogen, CN, $OR^7$, $N(R^7R^8)$, $S(O)pR^7$, NO, or $CF_3$;

$R^4$ is $CO_2R^7$, $CON(R^7R^8)$, CN, $S(O)pR^7$ or $COR^7$;

$R^5$ is $CO_2R^7$, $CON(R^7R^8)$, CN, $OR^7$, $N(R^7R^8)$, $S(O)pR^7$, F, Cl, Br, NO, $COR^7$, or $CF_3$;

$R^7$ and $R^8$ independently are H, or alkyl of 1–6 carbons;

W is pyridyl, pyrimidinyl, tetrahydrofuranyl;

m is 1 to 4;

n is 1 to 6; and p is 1 or 2.

14. A pharmaceutical cmposition of claim 12 wherein the compound is 1,3-Dihydro-1-phenyl-3,3-bis(4-pyridinylmethyl)-2H-pyrrolo[2,3-b]pyridin-2-one Dihydrochloride.

15. A pharmaceutical composition of claim 12 wherein the compound is 1,3-Dihydro-1-(4-chlorophenyl)-3,3-bis(4-pyridinylmethyl)-2H-pyrrolo [2,3-b]pyridin-2-one Dihydrochloride.

16. A pharmaceutical composition of claim 12 wherein the compound is 1,3-Dihydro-1-(4-chlorophenyl)-3-(3-cyanophenyl)-3-(4-pyridinylmethyl)-2H-pyrrolo[2,3-b]pyridin-2-one Dihydrochloride.

17. A pharmaceutical composition of claim 12 wherein the compound is 1,3-Dihydro-1-(4-chlorophenyl)-3-(3-pyridinylmethyl)-3-(4-pyridinylmethyl)-2H-pyrrolo[2,3-b]pyridin-2-one Dihydrochloride.

18. A pharmaceutical composition of claim 12 wherein the compound is 1,3-Dihydro-1-(4-chlorophenyl)-3-(phenylmethyl)-3-(4-pyridinylmethyl)-2H-pyrrolo[2,3-b]pyridin-2-one.

19. A method of treating cognitive disorders in a mammal, aid method comprising administering to a mammal in need of such treatment a therapeutically effective amount of a compound of the formula

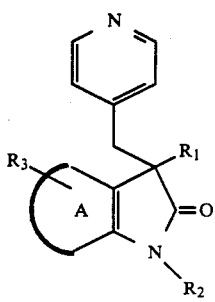

Formula I or a pharmaceutically acceptable salt thereof where A is a heteroaromatic system selected from the group consisting of

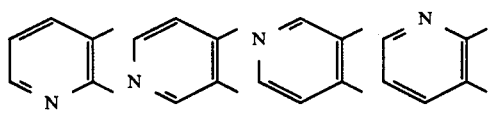

and wherein

R¹ is (CH₂)m-W or (CH₂)n-R⁴;
R² is alkyl of 1-7 atoms, benzyl substituted with 0-3 R⁴, or phenyl substituted with 0-3 R⁵;
R³ is H, alkyl of 1-6 carbon atoms, halogen, CN, OR⁷, N(R⁷R⁸), S(O)pR⁷, NO₂, or CF₃;
R⁴ is CO₂R⁷, CON(R⁷R⁸), CN, OR⁷, N(R⁷R⁸), S(O)pR⁷, F Cl, Br, NO₂, or COR⁷;
R⁵ is CO₂R⁷, CON(R⁷R⁸), CN, OR⁷, N(R⁷R⁸), S(O)pR⁷, F, Cl, Br, NO₂, COR⁷, or CF₃;
R⁷ and R⁸ independently are H, or alkyl of 1-6 carbon atoms;
W is pyridyl, pyrimidinyl, pyrazinyl, pyridazinyl, pyrazolyl, tetrahydrofuranyl, thienyl, or phenyl optionally substituted with 0-2 R⁵;
m is 1 to 4;
n is 1 to 6; and
p is 0 to 2.

20. The method of claim 19 wherein the compounds of formula

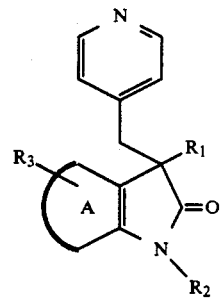

Formula I or a pharmaceutically acceptable salt thereof, wherein A is

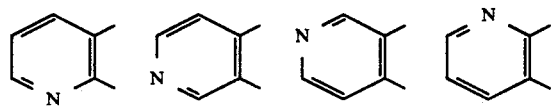

R¹ is (CH₂)m-W or (CH₂)n-R²;
R² is alkyl of 1-7 carbon atoms, benzyl substituted with 0-3 R⁴, or phenyl substituted with 0-3 R⁵;
R³ is H, alkyl of 1-6 carbon atoms, halogen, CN, OR⁷, N(R⁷R⁸), S(O)pR⁷, NO₂, or CF₃;
R⁴ is CO₂R⁷, CON(R⁷R⁸), CN, OR⁷, N(R⁷R⁸), S(O)pR⁷, F, Cl, Br, NO₂, or COR⁷;
R⁵ is CO₂R⁷, CON(R⁷R⁸), CN, OR⁷, N(R⁷R⁸), S(O)pR⁷, F, Cl, Br, NO₂, COR⁷, or CF₃;
R⁷ and R⁸ independently are H, or alkyl of 1-6 carbon atoms;
W is pyridyl, pyrimidinyl, pyrazinyl, pyridazinyl, pyrazolyl, tetrahydrofuranyl, thienyl, or phenyl optionally substituted with 0-2 R⁵;
m is 1 to 4;
n is 1 to 6; and
p is 0 to 2.

21. The method of claim 20 wherein the compound is of the formula

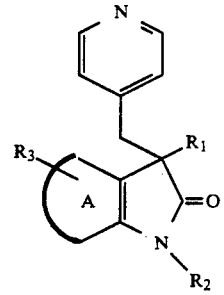

Formula I or a pharmaceutically acceptable salt thereof, wherein A is

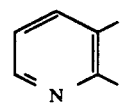

R¹ is (CH₂)m-W or (CH₂)n-R⁴;
R² is alkyl of 1-7 carbon atoms, benzyl substituted with 0-3 R⁴, or phenyl substituted with 0-3 R⁵;

$R^3$ is H, alkyl of 1–4 carbons, halogen, CN, $OR^7$, $N(R^7R^8)$, $S(O)pR^7$, $NO_2$, or $CF_3$;

$R^4$ is $CO_2R^7$, $CON(R^7R^8)$, CN, $S(O)pR^7$, or $COR^7$;

$R^5$ is $CO_2R^7$, $CON(R^7R^8)$, CN, $OR^7$, $N(R^7R^8)$, $S(O)pR^7$, F, Cl, Br, $NO_2$, $COR^7$, or $CF_3$;

$R^7$ and $R^8$ independently are H, or alkyl of 1–6 carbons;

W is pyridyl, pyrimidinyl, tetrahydrofuranyl;

m is 1 to 4;

n is 1 to 6; and p is 1 to 2.

22. The method of claim 21 wherein the compound is selected from the group consisting of 1,3-Dihydro-1-phenyl-3,3-bis(4-pyridinylmethyl)-2H-pyrrolo[2,3-b]pyridin-2-one Dihydrochloride.

1,3-Dihydro-1-(4-chlorophenyl)-3,3-bis(4-pyridinylmethyl)-2H-pyrrolo[2,3-b]pyridin-2-one Dihydrochloride, 1,3-Dihydro-1-(4-chlorophenyl)-3-(3-cyanophenyl)-3-(4-pyridinylmethyl)-2H-pyrrolo[2,3-b]pyridin-2-one Dihydrochloride, 1,3-Dihydro-1-(4-chlorophenyl)-3-(3-pyridinylmethyl)-3-(4-pyridinylmethyl)-2H-pyrrolo[2,3-b]pyridin-2-one Dihydrochloride.

1,3-Dihydro-1-(4-chlorophenyl)-3-(phenylmethyl)-3-(4-pyridinylmethyl)-2H-pyrrolo[2,3-b]pyridin-2-one.

* * * * *